US00PP16616P2

(12) United States Plant Patent
Whitcomb

(10) Patent No.: US PP16,616 P2
(45) Date of Patent: Jun. 6, 2006

(54) CRAPEMYRTLE PLANT NAMED 'WHIT VIII'

(50) Latin Name: *Lagerstroemia indica*
Varietal Denomination: WHIT VIII

(75) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 100 days.

(21) Appl. No.: 11/042,434

(22) Filed: Jan. 25, 2005

(51) Int. Cl.
*A01H 5/00* (2006.01)

(52) U.S. Cl. ..... Plt./252
(58) Field of Classification Search ..... Plt./252
See application file for complete search history.

(56) References Cited

U.S. PATENT DOCUMENTS

PP4,182 P 1/1978 Chopin
PP4,183 P 1/1978 Chopin
PP4,184 P 1/1978 Chopin
PP4,185 P 1/1978 Chopin
PP5,302 P 10/1984 Chopin
PP6,365 P 11/1988 Whitcomb
PP6,383 P 11/1988 Whitcomb

*Primary Examiner*—Anne Marie Grunberg

(74) *Attorney, Agent, or Firm*—Streets & Steele; Frank J. Campigotto; Jeffrey L. Streets

(57) ABSTRACT

A new and distinct variety of crapemyrtle, *Lagerstroemia indica,* particularly distinguished by having a near constant flower show during the growing season from new flower buds that form in the same positions as flowers that age and fall away. The flowers are soft pink and the flower buds are green to purple. Inflorescences are between about 4 and about 20 inches tall and between about 4 and about 16 inches wide. The crapemyrtle is further characterized by an upright growth habit and leathery leaves that emerge glossy purple and change to dark green.

6 Drawing Sheets

Genus, species: *Lagerstroemia indica.*
Varietal denomination: Crapemyrtle 'WHIT VIII'.

BACKGROUND OF THE INVENTION

Field of the Invention

The present invention relates to a new and distinct variety or cultivar of the ornamental shrub, *Lagerstroemia indica*, commonly known as crapemyrtle.

Description of the Related Art

Crapemyrtle is native to eastern China and was introduced into North America in the late 1700's. Since then, this popular ornamental shrub has been grown extensively across the southern half of the continent. Over the years, seedlings of *Lagerstroemia indica* have been selected and introduced into the market with different growth habits and flower colors. In addition, hybrids between *L. indica* and *L. fauriei* have been selected to add additional features, particularly more striking bark color.

The common name for the crapemyrtle is "crapemyrtle", not "crape myrtle". This is because the crapemyrtle is in the genus *Lagerstroemia* and in the Lythraceae plant family, and not in the genus *Myrtus,* which is in the Myrtaceae family. The crapemyrtle is simply a plant that looks, somewhat remotely, like a myrtle. On the other hand, the Greek myrtle, *Myrtus communis,* is a true myrtle and appropriately, the common name is two words.

In the preface of the book Standardized Plant Names, further insights are provided on this topic. "In the case of compound names in which a name properly belonging to one genus is applied in compound to a different genus, like horsechestnut or mayapple,failure to write or print them as compound words, either with a hyphen or solid is in many cases likely to cause serious confusion and should be consistently avoided. The committee prefers and prints mayapple. It makes no serious objection to may-apple. It objects very postively to may apple, which is apt to mean, for anyone not familiar with the plant, that it is a species or variety of the genus *Malus*." See, American Joint Committee on Horticulture Nomenclature. Kelsey, H. P., W. A. Dayton, Editors, *Standardized Plant Names,* 2$^{nd}$ Ed., p. vii, J. H. McFarland Co., Harrisburg, Pa. (1942).

The United States Department of Agriculture identifies the common name of *Lagerstroemia indica* as crapemyrtle. See, The USDA, NRCS. 2004. The PLANTS Database, Version 3.5 (http://plants.usda.gov). National Plant Data Center, Baton Rouge, La. 70874-4490 USA.

An assortment of methods has been utilized to develop improved varieties of crapemyrtle and several have had U.S. Plant Patents issued. For example, U.S. Plant Patents Nos. 4,182, 4,183, 4,184 and 4,185 disclose and claim a series of four new varieties of *Lagerstroemia indica* produced by crossing previously known varieties. Each of these varieties was characterized as having a weeping growth habit at maturity. U.S. Plant Pat. No. 5,302 also discloses a new variety of crapemyrtle exhibiting a weeping growth habit at maturity.

U.S. Plant Pat. Nos. 6,365 and 6,383 disclose varieties of crapemyrtle derived from seedlings treated with a mutationinducing chemical. It is generally known that sodium azide, colchicines and other chemicals are capable of producing plant mutations. Since one or more of the grandparents of the new variety of crapemyrtle was treated with one of these compounds, the present invention may be such a mutation.

The new variety of crapemrytle claimed herein, which has been given the cultivar name 'WHIT VIII', was selected from over 175,000 crapemyrtle seedlings grown from a selected seedling parent through eight generations. Seed resulting in the female grandparent of the present invention had been treated with sodium azide and colchicines known to induce mutations.

The crapemyrtle of the present invention was selected from about 1,350 seedlings grown from a $7^{th}$ generation seedling plant from when this research began in 1986. The parent was selected for exceptional growth and prolific white flowers that produced a modest number of viable seeds. The male parent is not specifically known because pollination resulted from natural insect activity among hundreds of seedlings adjacent to the female plant. Since no attempt was made to control pollination, pollen could have come from any of the surrounding crapemyrtle in the fields.

This new and distinct crapemyrtle was asexually reproduced by rooting softwood cuttings from the original 'WHIT VIII' plant near Stillwater, Okla. The asexually reproduced plants show the unique features that characterize this crapemyrtle indicating that the unique features of this plant are stable through its successive generations of asexual reproduction. The softwood cuttings taken from my new variety of crapemyrtle were successfully rooted under intermittent mist. Subsequent cuttings from plants produced from the previous cuttings of the 'WHIT VIII' original parent have been rooted and are identical to the orginal plant. Growth, flowering, flower and foliage color and the capacity to rebloom on old inflorescences remain consistent with the parent.

SUMMARY OF THE INVENTION

The plant of the present invention is a new and distinct variety of crapemyrtle, *Lagerstroemia indica,* which has been given the cultivar name 'WHIT VIII' and is characterized by a vigorous, upright growing, large shrub or small tree with moderate branching that may reach a height of between about 10 and 15 feet at maturity.

Leaves of the plant emerge dark purple and slowly change to dark green with age with midveins retaining some purple color when mature leaves are in full sun. Mature leaves are larger and more leathery than is typical of the species. Twigs of a current season's growth are distinctly purple unless heavily shaded by leaves and other branches.

Inflorescences are between about 4 and about 20 inches tall and between about 4 and about 16 inches wide. Flower buds are green when shaded but crimson when exposed to direct sun. Individual flowers are soft pink with little flower color change with age, until old flowers drop cleanly. Stamens are prominent and bright yellow in a few flowers but stamens in most flowers remain congested in the flower bud and never emerge.

Most flowers are sterile and produce no seed capsules. Only about 1% of the flowers produce seed capsules. To date, no viable seed have been produced in those capsules.

Each inflorescence typically produces a full flower show, then as the flowers age and fall, new flower buds form in the locations of the previous flowers. This unique feature creates a near continuous show of flowers during the growing season when not checked by drought or other environmental or cultural problems. Flowering typically begins in early July in North Central Oklahoma and flowering continues until frost.

DETAILED BOTANICAL DESCRIPTION

The following botanical description is of the new and distinct cultivar of crapemyrtle, *Lagerstroemia indica,* which has been given the cultivar name 'WHIT VIII'. Specific color designations set forth by number designations are in accordance with The Royal Horticultural Society Colour Chart (1966). General color recitations are consistent with ordinary American color terminology.

The crapemyrtle 'WHIT VIII' has not been observed under all possible environmental conditions. It is to be understood that the phenotype may vary significantly with variations in environment such as soils, temperature, light intensity and length of day without differences in the genotype of the plant. The following botanical characteristics and observations are taken from the plant when grown under normal outdoor conditions in north central Oklahoma. Unless otherwise noted, the following description is of the original parent plant, about 4 years old, growing in a field near Stillwater, Okla., but is also consistent with plants ranging from a few months to 16 months growing in containers in North Central Oklahoma.

The plant:

*Type.*—Deciduous woody shrub or small tree with single or multiple stems having an upright growth habit with moderate branching.

*Classification.*—Crapemyrtle, *Lagerstroemia indica.*

Figure 2:
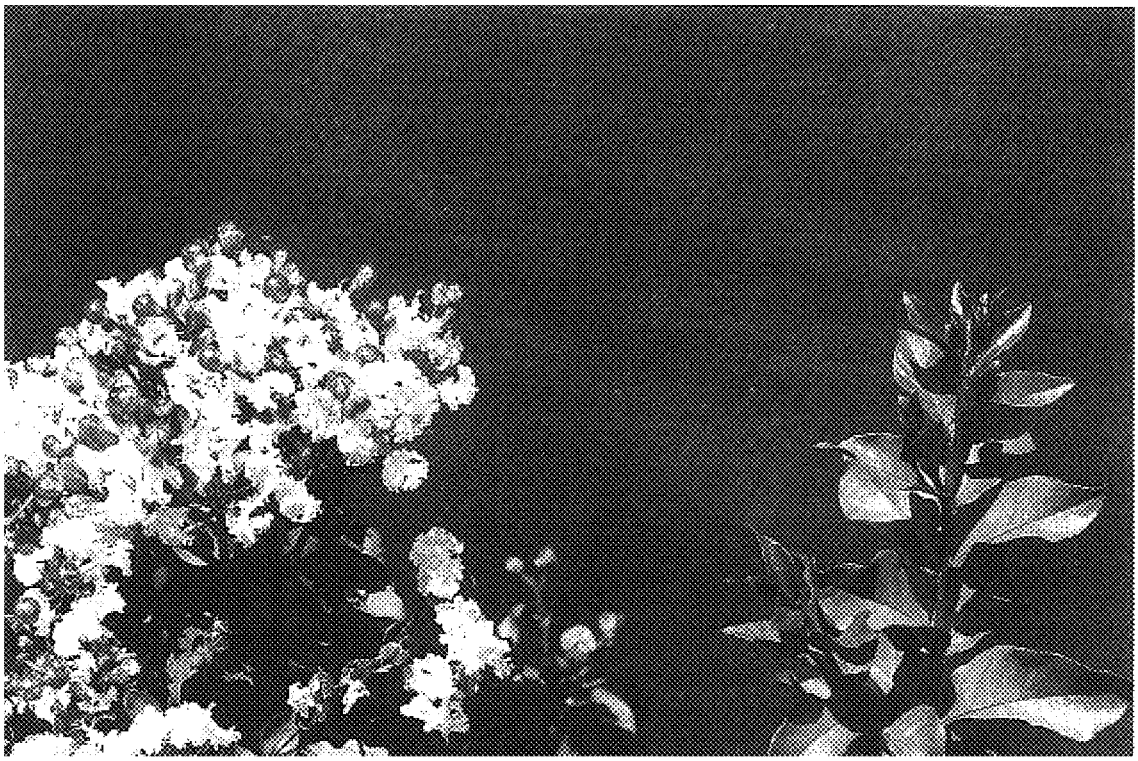
FIG. 2 is a full color photographic view of an inflorescence in full flower with new vegetative growth on the same plant.

*Growth habit.*—The plant is a vigorous upright grower when young. Vegetative growth is rapid in spring and continues until summer when flowering begins. Unlike other crapemyrtle varieties resulting from this breeding program such as U.S. Plant Pat. Nos. 10,296 and 10,342, which produce little new growth once flowering begins, WHIT VIII of the present invention typically produces new vegetative growth adjacent to full flowering inflorescences as shown in FIG. 2.

*Origin.*—an open pollinated cross in a crapemyrtle selection/breeding program in Stillwater, Okla.

*Propagation.*—The plant is easy to propagate from softwood cuttings with the distinguishing characteristics of the asexually propagated offspring remaining identical to the parent.

*Size and shape.*—The selected plants reached about 4.5 feet tall one year after a cutting was taken from the initially discovered WHIT VIII. Based upon the growth rate of the original WHIT VIII, it is estimated that the mature height may be between about 10 and about 15 feet with a spread of between about 8 and about 10 feet.

*Hardiness.*—The new variety of crapemyrtle has withstood temperatures of about 4° F. with no injury.

*Pests and disease.*—The foliage has been very resistant to powdery mildew.

Figure 4:
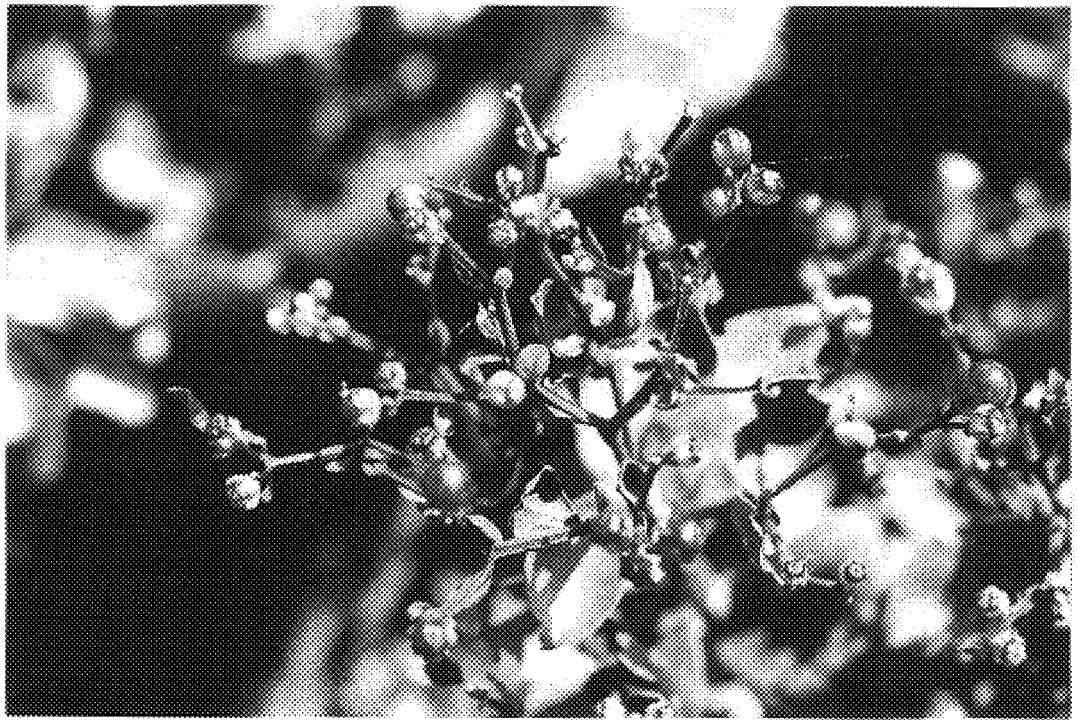
FIG. 4 is a full color photographic view of new flower buds developing on an inflorescence that has already produced one set of flowers.
Figure 5:
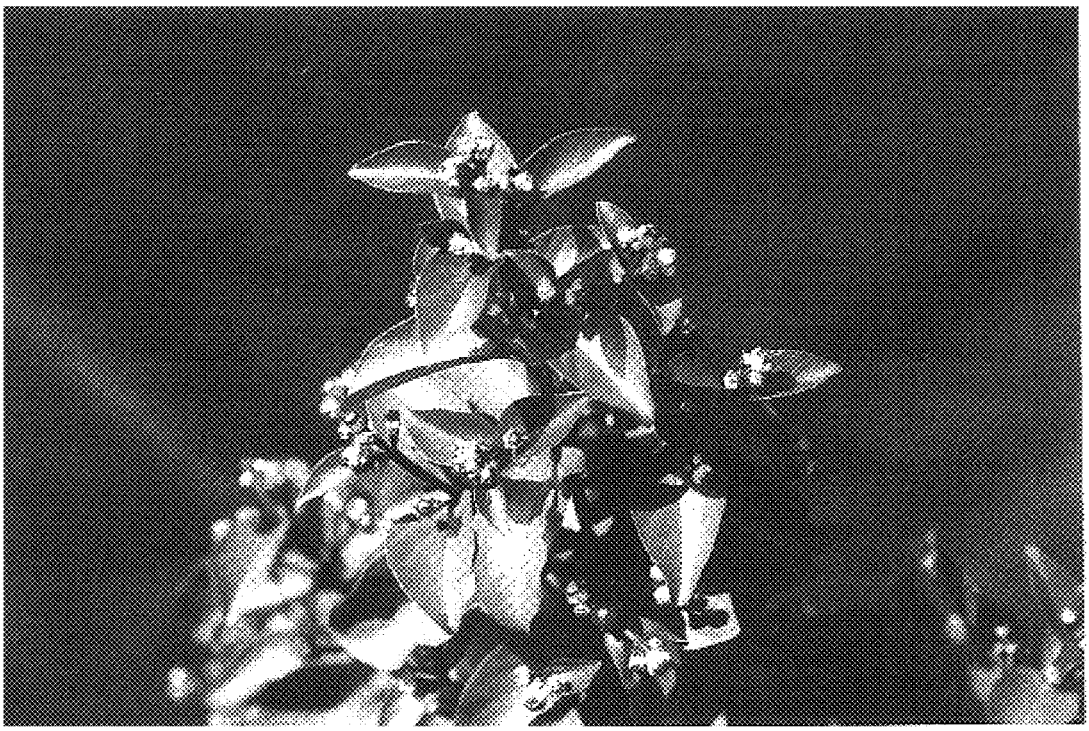
FIG. 5 is a full color photographic view of flower buds developing among purple new leaves during rapid new growth in mid summer.

The flowers:

*Blooming period.*—Blooming begins in early July and continues into October at frost in North Central Oklahoma. This flowering period is longer than most seedlings and cultivars of crapemyrtle known to me. Flowering continues during periods of intense and prolonged heat as long as moisture is available. Because the plant is sterile, after flowers age and fall from positions in the inflorescence, new flower buds are produced in the same location as shown in FIG. 4. Typically, two sets of flowers are produced on each inflorescence. This unusual flower production makes the flower show almost continuous and removes the peaks and valleys of flower show of conventional crapemyrtle. Flowers typically remain attractive for 10 to 15 days unless moisture is severely limiting.

*Petals.*—Blades of individual petals (expanded apical portion) are soft pink (186-B or C or 185-D or 64-D). The petal claw (the narrow stalk-like basal portion of the petal) is slightly darker pink (186-A or B). The flower petals, typically 6 but occasionally 5, open fully. As the flowers age, the flowers typically fall cleanly from the inflorescence without discoloring or becoming unattractive.

Figure 1:
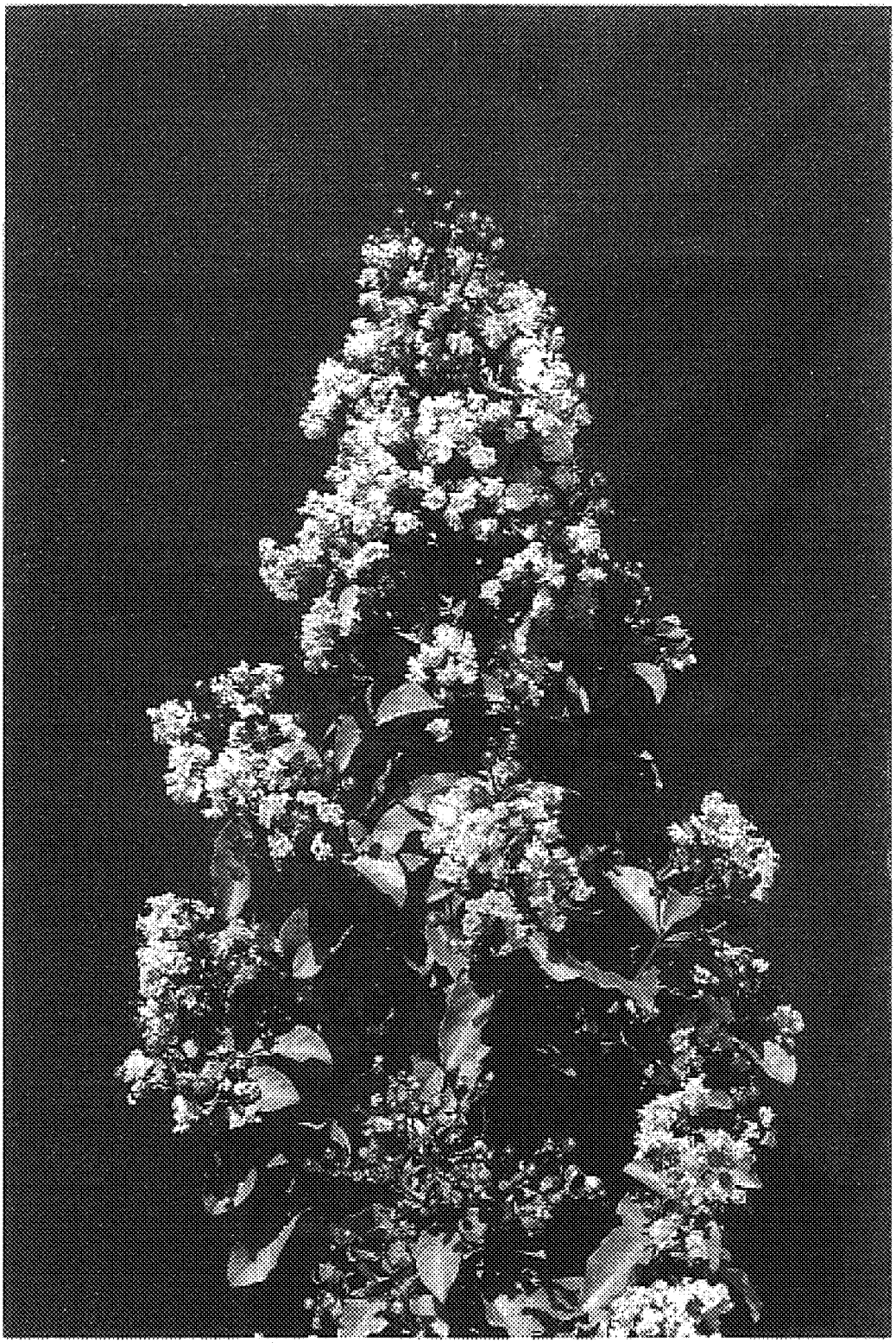
FIG. 1 is a full color photographic view of my new crapemyrtle plant, 'WHIT VIII', showing its growth and flowering near Stillwater, Okla.

*Inflorescences.*—The inflorescences are panicles between about 4 and about 20 inches tall and between about 4 and about 16 inches wide as shown in FIG. 1. The stocks of inflorescences exposed to full sun are purplish (187-A or B).

Figure 3:
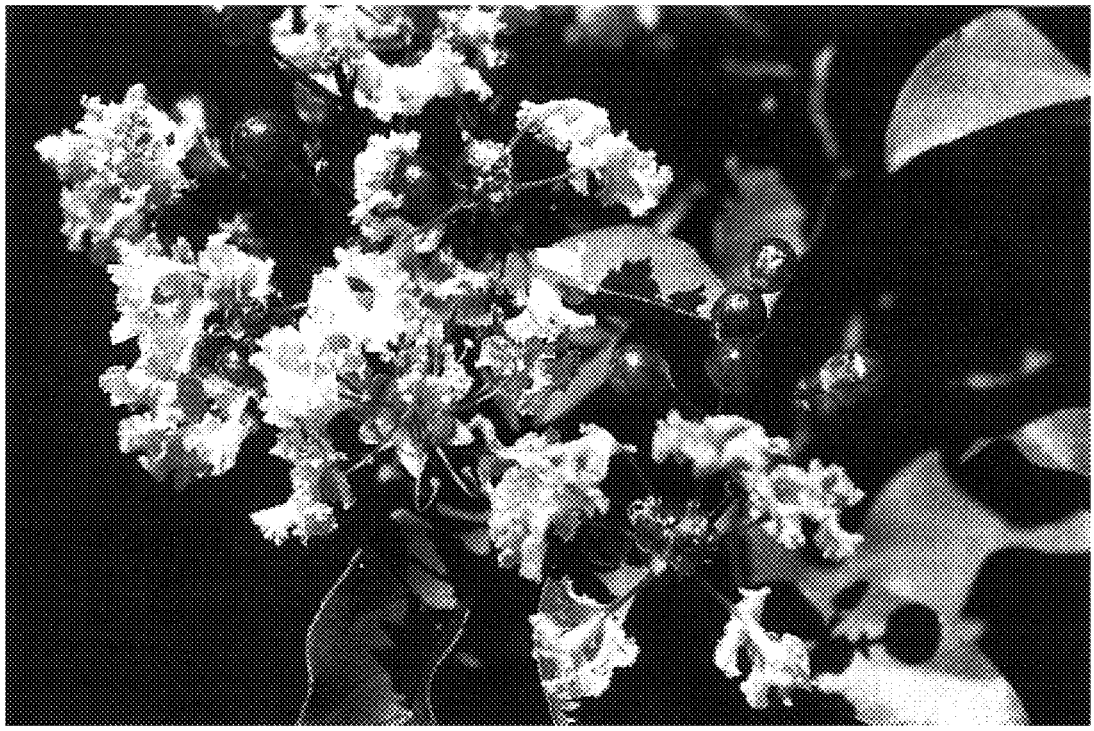
FIG. 3 is a full color photographic view of crimson flower buds and open flowers, one with exposed yellow stamens while the others have no fully expanded stamens.

*Stamens.*—An occasional flower has distinct yellow stamens (15-A), but more common are a complex of twisted and deformed stamens mostly retained in the flower bud as shown in FIG. 3.

*Sepals.*—There are six sepals per bloom, each having the shape of one-sixth of a sphere.

*Buds.*—Unopened flower buds are round with six distinct lines of dehiscence where they split to allow flower petals to expand. Bud size increases with age to typically between about 3/16 and about 5/16 inch diameter. The unopened flower buds are variable, purple-crimson (187-A) in direct sun and particularly along the lines of dehiscence, with a transition to a lighter purple-crimson (187-B or C) between the lines and with less direct sun. Portions of flower buds not exposed to sun are typically bright green (143-B or C).

*Seeds.*—The plant is nearly sterile. Counts of flowers in an inflorescence followed by counts of seed capsules produced revealed that only about 1% of the flowers produce a seed capsule. To date no viable seed have been produced. Immature seed capsules are dark yellow green (146-A or B) while mature capsules are dark brown (177-A or B).

Figure 6:
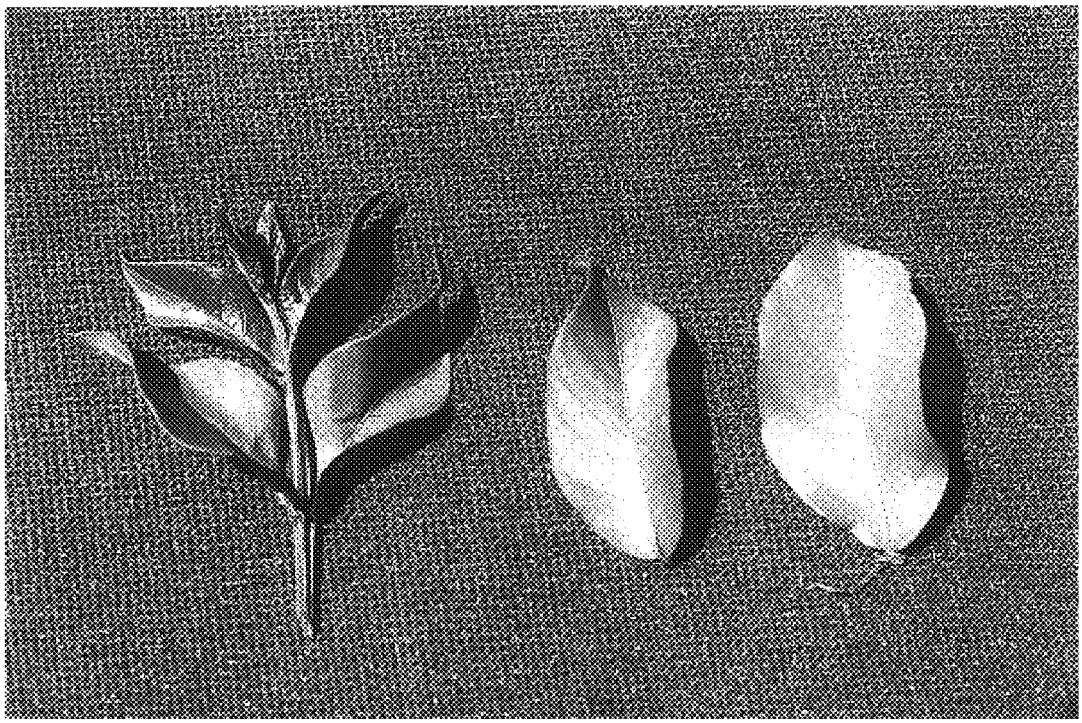
FIG. 6 is a full color photographic view of leaves ranging from very new at left to fully mature leaves at right.

The foliage:

*Leaf shape.*—The leaf shapes range from obtuse, acute to slightly acuminate at the tip and obtuse to slightly acute at the base as shown in FIG. 6. The leaf petiole is typically absent or very short and not distinct.

*Leaf color.*—The upper and lower surfaces of new leaves emerge glossy dark purple, grayed-purple (group 187-A) and remain so for two weeks or more with a gradual transition to green with age and maturity as shown in FIG. 6. Foliage color varies with light intensity and growing conditions.

*Upper leaf surface.*—Upper surfaces of mature leaves exposed to sun are dark green (147-A) with only faint traces of the earlier purple color but mid veins remain dark grayish purple (187-A or B).

*Under leaf surface.*—Under surfaces of mature leaves are green (147-A or B) with mid veins of dark grayish purple (187-B or C).

*Leaf texture.*—Mature leaves are thick and leathery.

*Leaf size.*—The leaf size is larger than the species average, varying from between about 1.0 and about 2.75 inches long by between about 0.5 and about 1.5 inches wide, with the widest point approximately at the center.

The branches and bark:

*Branch color.*—Current season's stems, exposed to direct light are purple, grayed-purple (187-A). As stems age, there is a color transition to a lighter grayed purple (187-B, C or D) and finally to medium brown (177-B, C or D).

*Branch length.*—The branch length is dependent upon the growing coditions of the plant, typically ranging from between about 4 inches and to more than about 36 inches long.

*Branch diameter.*—The diameter of a current season's growth ranges from between about 3/32 and about 15/32 inch.

*Bark.*—The bark is typical of *L. indica* species and is exfoliating. Four year old stems that have exfoliated range from light brown (199-A or B) when shaded or medium gray green (197-A or B) when exposed to sun.

I claim:

1. A new and distinct variety of crapemyrtle plant, substantially as illustrated and described.

* * * * *